(12) United States Patent
Delmonico et al.

(10) Patent No.: US 8,310,604 B2
(45) Date of Patent: Nov. 13, 2012

(54) VISUAL INSPECTION APPARATUS HAVING LIGHT SOURCE BANK

(75) Inventors: James J. Delmonico, Baldwinsville, NY (US); Marjorie L. Buerkle, Skaneateles, NY (US); Thomas W. Karpen, Skaneateles, NY (US); Joseph V. Lopez, Camillus, NY (US); Joshua Lynn Scott, Jordan, NY (US); Dennis W. McEnery, Marcellus, NY (US)

(73) Assignee: GE Sensing & Inspection Technologies, LP, Lewistown, PA (US)

( * ) Notice: Subject to any disclaimer, the term of this patent is extended or adjusted under 35 U.S.C. 154(b) by 1331 days.

(21) Appl. No.: 11/925,090

(22) Filed: Oct. 26, 2007

(65) Prior Publication Data

US 2009/0109431 A1    Apr. 30, 2009

(51) Int. Cl.
*A61B 1/04*     (2006.01)
*H04N 5/74*     (2006.01)
(52) U.S. Cl. .......................................... 348/748; 348/68
(58) Field of Classification Search .......... 327/512–513; 600/101, 118; 348/76, 748–749, 68
See application file for complete search history.

(56) References Cited

U.S. PATENT DOCUMENTS

| 4,700,693 A | 10/1987 | Lia et al. |
| 4,727,859 A | 3/1988 | Lia |
| 4,733,937 A | 3/1988 | Lia et al. |
| 4,735,501 A | 4/1988 | Ginsburgh et al. |
| 4,787,369 A | 11/1988 | Allred, III et al. |
| 4,790,294 A | 12/1988 | Allred, III et al. |
| 4,794,912 A | 1/1989 | Lia |
| 4,796,607 A | 1/1989 | Allred, III et al. |
| 4,853,774 A | 8/1989 | Danna et al. |
| 4,862,253 A | 8/1989 | English et al. |
| 4,887,154 A | 12/1989 | Wawro et al. |
| 4,901,142 A * | 2/1990 | Ikuno et al. ..................... 348/69 |
| 4,909,600 A | 3/1990 | Ciarlei et al. |
| 4,913,369 A | 4/1990 | Lia et al. |
| 4,941,454 A | 7/1990 | Wood et al. |
| 4,941,456 A | 7/1990 | Wood et al. |
| 4,980,763 A | 12/1990 | Lia |
| 4,989,581 A | 2/1991 | Tamburrino et al. |
| 4,998,182 A | 3/1991 | Krauter et al. |
| 5,018,436 A | 5/1991 | Evangelista et al. |
| 5,018,506 A | 5/1991 | Danna et al. |
| 5,019,121 A | 5/1991 | Krauter |
| 5,047,848 A | 9/1991 | Krauter |
| 5,052,803 A | 10/1991 | Krauter |
| 5,061,995 A | 10/1991 | Lia et al. |
| 5,066,122 A | 11/1991 | Krauter |
| 5,070,401 A | 12/1991 | Salvati et al. |
| 5,114,636 A | 5/1992 | Evangelista et al. |

(Continued)

FOREIGN PATENT DOCUMENTS

EP    573158 A1 * 12/1993

*Primary Examiner* — Brendan Higa
(74) *Attorney, Agent, or Firm* — Global Patent Operation; Mark A. Conklin

(57) ABSTRACT

A visual inspection apparatus can include a handset, elongated inspection tube extending from the handset and a light source bank disposed within a hand held housing of the handset. For reduction of heat energy radiating from the light source bank, the apparatus can include one or more of a thermal control system and a particularly designed heat sink assembly.

19 Claims, 9 Drawing Sheets

U.S. PATENT DOCUMENTS

| | | | |
|---|---|---|---|
| 5,136,397 A * | 8/1992 | Miyashita | 348/748 |
| 5,140,975 A | 8/1992 | Krauter | |
| 5,191,879 A | 3/1993 | Krauter | |
| 5,202,758 A | 4/1993 | Tamburrino | |
| 5,203,319 A | 4/1993 | Danna et al. | |
| 5,275,152 A | 1/1994 | Krauter et al. | |
| 5,278,642 A | 1/1994 | Danna et al. | |
| 5,314,070 A | 5/1994 | Ciarlei | |
| 5,323,899 A | 6/1994 | Strom et al. | |
| 5,345,339 A | 9/1994 | Knieriem et al. | |
| 5,347,989 A | 9/1994 | Monroe et al. | |
| 5,365,331 A | 11/1994 | Tamburrino et al. | |
| 5,373,317 A | 12/1994 | Salvati et al. | |
| D358,471 S | 5/1995 | Cope et al. | |
| 5,435,296 A | 7/1995 | Vivenzio et al. | |
| 5,633,675 A | 5/1997 | Danna et al. | |
| 5,701,155 A | 12/1997 | Wood et al. | |
| 5,734,418 A | 3/1998 | Danna | |
| 5,754,313 A | 5/1998 | Pelchy et al. | |
| 5,760,636 A * | 6/1998 | Noble et al. | 327/513 |
| 5,857,963 A | 1/1999 | Pelchy et al. | |
| 5,879,289 A * | 3/1999 | Yarush et al. | 600/179 |
| 5,974,557 A * | 10/1999 | Thomas et al. | 713/322 |
| 6,068,592 A * | 5/2000 | Davis | 600/132 |
| 6,083,152 A | 7/2000 | Strong | |
| 6,097,848 A | 8/2000 | Salvati | |
| 6,134,667 A * | 10/2000 | Suzuki et al. | 713/300 |
| 6,213,998 B1 * | 4/2001 | Shen et al. | 606/10 |
| 6,216,235 B1 * | 4/2001 | Thomas et al. | 713/501 |
| 6,333,602 B1 * | 12/2001 | Kayser | 315/117 |
| 6,432,046 B1 * | 8/2002 | Yarush et al. | 600/179 |
| 6,468,201 B1 | 10/2002 | Burdick | |
| 6,483,535 B1 | 11/2002 | Tamburrino et al. | |
| 6,494,739 B1 | 12/2002 | Vivenzio et al. | |
| 6,538,732 B1 | 3/2003 | Drost et al. | |
| 6,554,765 B1 | 4/2003 | Yarush et al. | |
| 6,590,470 B1 | 7/2003 | Burdick | |
| 6,830,545 B2 | 12/2004 | Bendall | |
| 6,847,394 B1 | 1/2005 | Hansen et al. | |
| 6,953,432 B2 | 10/2005 | Schiefer | |
| 7,048,686 B2 | 5/2006 | Kameya et al. | |
| 7,134,993 B2 | 11/2006 | Lia et al. | |
| 7,170,677 B1 | 1/2007 | Bendall et al. | |
| 7,262,797 B2 | 8/2007 | Weldum et al. | |
| 7,914,448 B2 * | 3/2011 | Bob et al. | 600/175 |
| 7,976,462 B2 * | 7/2011 | Wright et al. | 600/171 |
| 2002/0045801 A1 * | 4/2002 | Niida et al. | 600/118 |
| 2003/0035107 A1 * | 2/2003 | Overbeck et al. | 356/405 |
| 2003/0212308 A1 | 11/2003 | Bendall | |
| 2004/0176823 A1 * | 9/2004 | Island et al. | 607/88 |
| 2004/0183900 A1 | 9/2004 | Karpen et al. | |
| 2004/0215413 A1 | 10/2004 | Weldum et al. | |
| 2004/0233318 A1 | 11/2004 | Schiefer | |
| 2005/0050707 A1 | 3/2005 | Scott et al. | |
| 2005/0129108 A1 | 6/2005 | Bendall et al. | |
| 2005/0162643 A1 | 7/2005 | Karpen | |
| 2005/0165275 A1 | 7/2005 | Von Felten et al. | |
| 2005/0168571 A1 | 8/2005 | Lia et al. | |
| 2005/0281520 A1 * | 12/2005 | Kehoskie et al. | 385/117 |
| 2006/0050983 A1 | 3/2006 | Bendall et al. | |
| 2006/0072903 A1 | 4/2006 | Weldum et al. | |
| 2006/0155168 A1 | 7/2006 | Pease | |
| 2006/0167340 A1 | 7/2006 | Pease et al. | |
| 2006/0181878 A1 | 8/2006 | Burkholder | |
| 2007/0030344 A1 | 2/2007 | Miyamoto et al. | |
| 2007/0070340 A1 | 3/2007 | Karpen | |
| 2007/0091183 A1 | 4/2007 | Bendall et al. | |
| 2007/0112253 A1 * | 5/2007 | Negishi | 600/118 |
| 2007/0129604 A1 | 6/2007 | Hatcher et al. | |
| 2007/0156018 A1 | 7/2007 | Krauter et al. | |
| 2007/0156021 A1 | 7/2007 | Morse et al. | |
| 2007/0165306 A1 | 7/2007 | Bendall et al. | |
| 2007/0187574 A1 | 8/2007 | Lia | |
| 2007/0188604 A1 | 8/2007 | Miyamoto et al. | |
| 2007/0225561 A1 | 9/2007 | Watanabe et al. | |
| 2007/0225931 A1 | 9/2007 | Morse et al. | |
| 2007/0226258 A1 | 9/2007 | Lambdin et al. | |
| 2007/0249904 A1 | 10/2007 | Amano et al. | |
| 2007/0255100 A1 | 11/2007 | Barlow et al. | |
| 2008/0009677 A1 | 1/2008 | Shoroji et al. | |
| 2008/0021268 A1 | 1/2008 | Shoroji et al. | |
| 2008/0214896 A1 * | 9/2008 | Krupa et al. | 600/136 |
| 2008/0298831 A1 * | 12/2008 | VanKouwenberg et al. | 399/92 |
| 2009/0054768 A1 * | 2/2009 | Halmann et al. | 600/437 |
| 2009/0245839 A1 * | 10/2009 | Cook et al. | 399/69 |

* cited by examiner

US 8,310,604 B2

VISUAL INSPECTION APPARATUS HAVING LIGHT SOURCE BANK

CROSS REFERENCE TO RELATED APPLICATIONS

The present application is related to U.S. patent application Ser. No. 11/925,085 entitled, "Inspection Apparatus Having Heat Sink Assembly" filed concurrently herewith and incorporated by reference herein.

BACKGROUND OF THE INVENTION

The invention relates to inspection apparatuses generally and specifically to an inspection apparatus for inspecting articles.

Commercially available inspection apparatuses have been made available in form factors including components distributed into a plurality of different housings.

In one common form factor, components of a visual inspection apparatus can include a hand held portion and a spaced apart base unit each having a different associated housing. In the base unit, a light source bank might be incorporated together with various processing circuitry. In some known prior art visual inspection apparatus, a motorized fan might be incorporated in the base unit for cooling of the light source bank.

BRIEF DESCRIPTION OF THE INVENTION

A visual inspection apparatus can include a handset, an elongated inspection tube extending from the handset and a light source bank. For reduction of heat energy radiating from one or more components of the apparatus, the apparatus can include a thermal control system wherein a cooling procedure can be initiated responsively to a sensed temperature.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

DETAILED DESCRIPTION OF THE INVENTION

Figure 1:
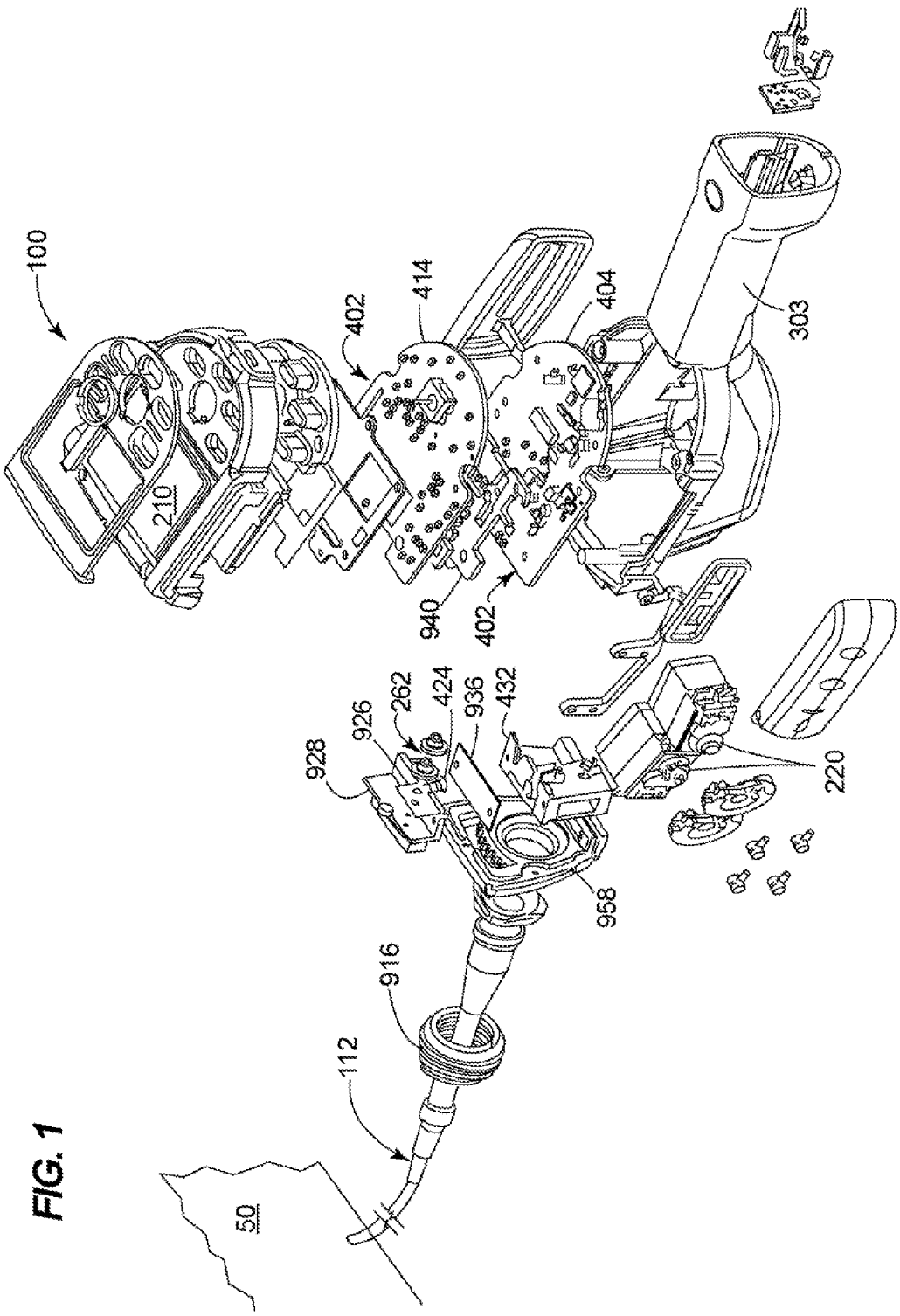
FIG. 1 is an exploded assembly view of an inspection apparatus in one embodiment.

There is described in one aspect, a visual inspection apparatus comprising a handset having a hand held housing, an elongated inspection tube extending from the handset and a light source bank. A light source bank can include one or more light sources. For reduction of heat energy radiating from one or more components of the apparatus, the inspection apparatus can include one or more of a thermal control system and a particularly designed heat sink assembly. According to a thermal control system in one embodiment, light source bank driver signals can be presented to the light source bank responsively to sensed temperature. The cooling procedure including presenting energy conserving light source bank driver signals can be replaced or supplemented with one or more alternative cooling procedures, e.g., a cooling procedure wherein energy conserving driver signals are applied to other electrical power consuming components of the apparatus.

The deployment of one or more of the thermal control or heat sinking system in a visual inspection apparatus facilitates that deployment of a light source bank and processing circuitry in a common hand held housing that is small enough to be carried in a human hand.

In one embodiment, a thermal control system can be incorporated in an inspection apparatus having at least one temperature sensor for sensing an internal temperature within a hand held housing of a handset. Responsively to a sensed temperature exceeding a threshold, the apparatus can initiate a cooling procedure for cooling of the interior temperature. In one embodiment a cooling procedure can include one or more of presenting an energy conserving light source bank driver signal to a light source bank within the hand held housing, presenting an energy conserving motor assembly driver signal to an articulation motor assembly within the hand held housing, and presenting an energy conserving illuminator driver signal to a display illuminator within the hand held housing.

In another embodiment, an inspection apparatus can be adapted so that the noted cooling procedures can be initiated in succession one after another should a first of the cooling procedures not be successful in yielding acceptable cooling according to a criteria. In another aspect the apparatus can be adapted so that an inspector user can designate an order (priority) of the cooling procedures to be initiated and can disable one or more of the cooling procedures so that cooling procedures designated as being disabled are prevented from being initiated even where high heat conditions are sensed.

In another aspect the apparatus can be adapted to accommodate use of a light source bank having a power consumption rating higher than a power consumption rating of one or a combination of processing electrical components within the hand held housing. To facilitate use of a light source bank having a power consumption rating higher than processing electrical components and to prevent processing electrical components from being subject to thermal damage by heat generated by a light source bank, the light source bank can be provided in thermal separation relative to the processing electrical components. Further, temperatures of the thermally separated electrical components can be separately sensed with separate temperature sensors and a thermal control system can be adapted to initiate one or more cooling procedures responsively to a temperature sensed by each of the sensors. In one example one or more cooling procedures can be initiated responsively to sensed temperature of a first sensor exceeding a first threshold and the one or more cooling procedures can further be initiated responsively to a sensed temperature of the second sensor exceeding a second threshold. In one embodiment, where a light bank components is to be maintained in thermal separation from a processing component, first and second sets of thermally separated heat sink members can be provided to carry heat from an interior of the hand held housing to an exterior of the hand held housing.

In a still further aspect, an inspection apparatus can include at least one heat sink member that is exposed to an exterior of the handset. An exposed heat sink member while useful in removing heat from an interior of the handset delimited by a hand held housing can be specially positioned so as to reduce an incidence of contact therewith by an inspector. In a further aspect a sensed temperature of an exposed heat sink member can be compared to a threshold for determination of whether a cooling procedure should be initiated. An inspection apparatus can be adapted so that if a sensed temperature of an exposed heat sink member that might be contacted by an inspector exceeds a threshold one or more cooling procedures can be initiated.

In yet another aspect heat sink members for carrying heat away from an interior of the handset can include components of an elongated inspection tube. In one embodiment one or more components of an elongated inspection tube can be provided in thermal communication with an electrical component of an interior of a handset. In such an embodiment, the noted components of the elongated inspection tube serve as components of the inspection tube and as components of a heat sink assembly.

In another aspect a heat sink member of the apparatus can include multiple fins. Fins of a multi-fin heat sink member can be of a configuration having a narrowing thickness from base to tip. In such configuration, heat conducted at the tip is limited, rendering the tip cooler to the touch.

In one embodiment, light source bank and one or more processing electrical circuit components within the hand held housing can be thermally separated to prevent the conduction of heat from a light source bank to processing circuitry component and to further facilitate the use of a higher lumens outputting light source bank.

In one embodiment, a heat sink assembly can be provided for removing heat from internal components of the hand held housing. A heat sink assembly can include a first plurality of heat sink members and a thermally separated second plurality of heat sink members. The first plurality of heat sink members can remove heat from the light source bank and the second thermally separated plurality of heat sink members can remove heat from processing circuitry components of the apparatus.

While a specific embodiment is described wherein a thermal control system and heat sink assembly are incorporated in a visual display system it will be seen that the technologies described can also be incorporated in other apparatuses such as an eddy current inspection apparatus and an ultrasonic inspection apparatus where it is desired to cool or remove heat from an apparatus. Elements of the described technologies relating to deployment of a light source bank in close proximity to processing circuitry will find use in any apparatus wherein a light source bank is disposed in close proximity to or is commonly housed in a common housing with processing circuitry.

An inspection apparatus 100 in one embodiment is shown and described in the physical form exploded assembly view of FIG. 1. Inspection apparatus 100 can include a two dimensional sensor 132 and a lens 140 (optics) for focusing images of a target substrate onto image sensor 132. Lens 140 can include, e.g., a lens singlet, a lens doublet, or a lens triplet. Handset 302, which can alternately be termed a hand held control and display module, can include a keyboard 214, a joystick 217, and a display 210 for display of electronic image representations (image data) representing images incident on image sensor 132. Inspection apparatus 100 can also include a light source bank 262 for illuminating a target substrate 50. Inspection apparatus 100 can further include an elongated inspection tube 112 extending outwardly from handset 302. Elongated inspection tube 112 can be adapted to transmit light from light source bank 262 so that such light can be projected from a distal end of elongated inspection tube 112 for illumination of a target substrate 50 (of an article being inspected). Light source bank 262 can include one or more light sources. In one embodiment, light source bank 262 comprises a single LED. In another embodiment, light source bank 262 comprises a plurality of LEDs. In a further aspect handset 302 can include a hand held housing 303 incorporating various electrical components of apparatus 100. In one embodiment, light source bank 262 for illuminating a target substrate 50 as well as processing circuitry can be incorporated within hand held housing 303. Referring ahead to the electrical block diagram of FIG. 4, every component depicted within dashed in border 1303 of FIG. 4 can be disposed within (in an interior of) hand held housing 303.

Referring to further aspects of an inspection apparatus in a particular embodiment, apparatus 100 can include a light source bank 262 carried by light source bank circuit board 424 and processing circuitry 402 carried by one or more processing printed circuit boards 404 and 414. Processing circuitry 402 can include one or more of image processing circuitry and control signal processing circuitry. Regarding image processing circuitry of processing circuitry 402, image processing circuitry can include e.g., circuitry for receipt of analog or digital image signals representing light incident on image sensor, circuitry for formatting such signals for display on display 210 in the formation of a streaming video image, circuitry for storage of image data into memory, and circuitry for formatting image data into a standardized image or raw video format and circuitry for transmitting image data to an external computer. Regarding control signal processing circuitry of processing circuitry 402, such circuitry can include e.g., circuitry for reading signals presented by sensors of apparatus 100 and/or control input devices and responsively outputting control signals to an output device or other component of apparatus 100. It will be seen that a single electrical component of apparatus 100, e.g., a single integrated line unit, such as a single DSP integrated circuit chip (e.g., chip 152 and chip 180 as described with reference to FIG. 4) can be both a component of the image processing circuitry and the control processing circuitry.

In one aspect, apparatus 100 can be adapted to sense a temperature of a circuit board of apparatus 100 and responsively to the sensed temperature present a light source bank driver signal to light source bank 262 and/or energy conserving driver signal to another component of apparatus 100. In one embodiment, apparatus 100 can be adapted to sense a temperature of both of first and second processing circuit boards 404 and 414 and light source bank circuit board 424.

Apparatus 100 can be adapted so that if a sensed temperature of one or more of circuit boards 404, 414, 424 exceeds a threshold, apparatus 100 responsively presents an energy conserving light source driver signal to one or more power consuming electrical components of apparatus 100, e.g., light source bank 262, illuminator 209, and/or motor assembly 220.

Figure 2:
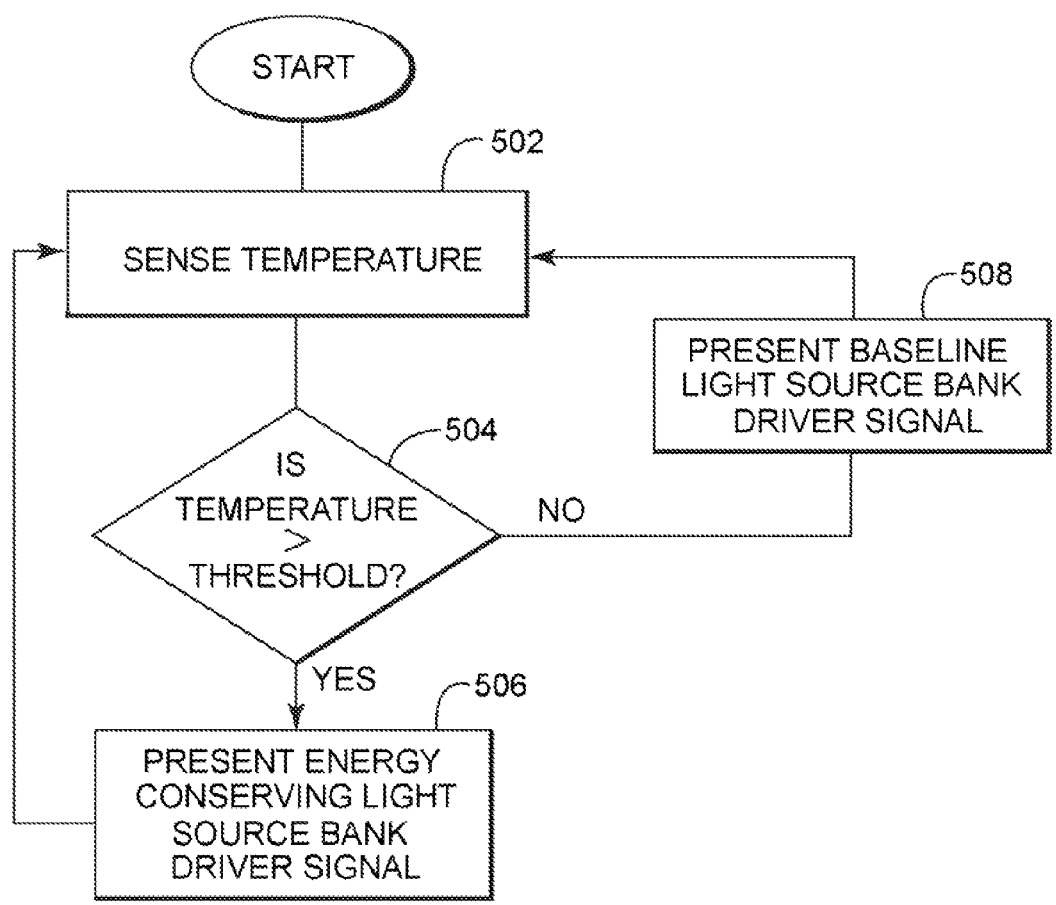
FIG. 2 is a flow diagram illustrating a method for thermal control in one embodiment.

A flow diagram illustrating a thermal control method is described further with reference to FIG. 2. At block 502, apparatus 100 can sense a temperature of one or more circuit boards (e.g., a processing circuit board 404, 414, or light source bank circuit board 424). At block 504, apparatus 100 can determine whether a sensed temperature sensed at block 502 exceeds a threshold, and at block 506 apparatus 100 can present a driver signal for driving light source bank 262 responsively to the sensed temperature. If a sensed temperature is above a threshold temperature, apparatus 100 at block 506 can present (apply) an energy conserving light source bank driver signal to light source bank 262. Alternatively, if a temperature of each of the one or more circuit boards is below a threshold, apparatus 100 at block 508 can present (apply) a baseline light source bank driver signal to light source bank 262. If the sensed temperature remains below a threshold, apparatus 100 can repetitively execute block 508 by maintaining an applied driver signal in accordance with a baseline driver signal. If a sensed temperature remains above a threshold, apparatus 100 can repetitively execute block 506 by maintaining a driver signal in accordance with an energy conserving driver signal.

Regarding circuit boards 424, 404, 414, circuit boards 424, 404, 414 can comprise thermally conductive circuit boards having one or more thermally conductive layers comprising thermally conductive material (e.g., copper).

Regarding block 502, apparatus 100 can sense a temperature of a circuit board 424, 404, 414 by reading a temperature indicating signal of a thermocouple disposed on circuit board 424, 404, 414. Apparatus 100 at block 502 can also sense a temperature of a circuit board 424, 404, 414 by examining characteristics of a signal output by a circuit component disposed on the printed circuit board. It will be understood that a temperature of a circuit board 404, 414 is a surrogate measure of processing circuitry or another component disposed on or in thermal communication with the circuit board 404, 414. Accordingly, the step of sensing a temperature of a circuit board can also be regarded to be a step of sensing a temperature of processing circuitry disposed on the circuit board. In one embodiment, a temperature of all three circuit boards 424, 404, 414 is sensed. In another embodiment, a temperature of only one of circuit boards 404, 414, 424 is sensed.

Regarding block 502, a "threshold" referred to at block 502 can be a predetermined threshold or a dynamic threshold that is variable depending on one or more of control inputs input by an inspector or additional sensed conditions. In one embodiment, a threshold utilized by apparatus 100 differs for each circuit board. For example, in one embodiment, apparatus 100 at block 502 can compare a sensed temperature of light source bank circuit board 424 to a first threshold for determining whether to adjust a light source bank driver signal, can compare a sensed temperature of processing circuit board 404 to a second threshold for determining whether to adjust a light source bank driver signal (e.g., to determine whether to present a baseline light source bank driver signal or an energy conserving light source bank driver signal), and can compare a sensed temperature of processing circuit board 414 to a third threshold for determining whether to adjust a light source bank driver signal.

Figure 3:
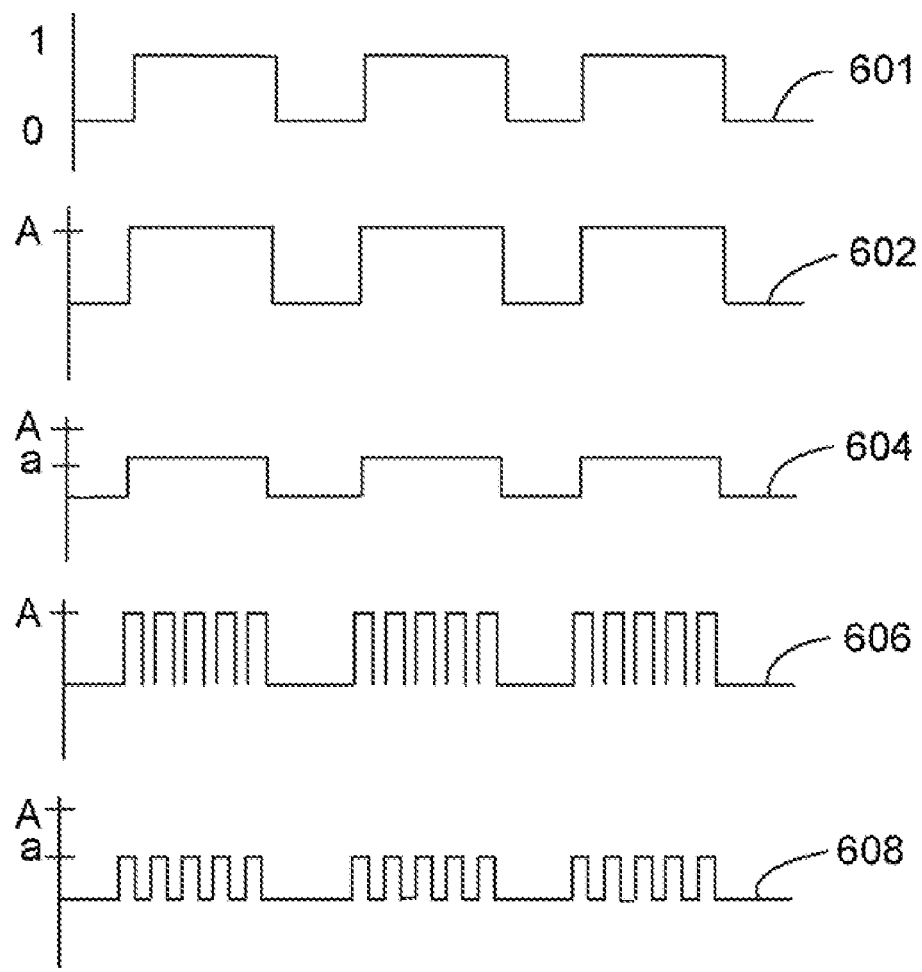
FIG. 3 is a timing diagram illustrating a thermal control method in one embodiment.

An example of method step 506 for adjusting a light source bank driver signal responsively to a sensed temperature is described further with reference to the timing diagram of FIG. 3. A baseline light source bank driver signal is represented by signal 602, characterized by peak power levels of amplitude A, and a maximum duty cycle during illumination on times coincident with exposure periods. Signal 602 represents a baseline light source bank driver signal presented to light source bank 262 under normal operation conditions where there is no overheating of any circuitry of apparatus 100 sensed. Baseline light source bank driver signal 602 can be coordinated with exposure control signal 601 also shown in the timing diagram of FIG. 3 so that light source bank driver signal 602 is in an energized state during exposure periods of apparatus 100 and is in a de-energized state intermediate of exposure periods.

Signal 604 represents an adjusted energy conserving setting of light source bank driver signal in one embodiment. In one embodiment, apparatus 100 can adjust a light source bank driver signal to exhibit the characteristics shown by energy conserving light source bank driver signal 604 responsively to a sensed temperature of one or more circuit boards 424, 404, 414, exceeding a threshold. Relative to signal 602, energy conserving light source bank driver signal 604 has a peak power level of reduced amplitude a, where a<A. Accordingly, the amount of heat radiating from light source bank 262 will be reduced as a result of a change in a setting of an applied light source bank driver signal from signal 602 to signal 604.

Signal 606 represents an energy conserving setting light source bank driver signal in one embodiment. In another embodiment, apparatus 100 can present a light source bank driver signal in accordance with the characteristics shown by signal 606 responsively to a sensed temperature of one or more circuit boards 424, 404, 414 exceeding a threshold. Relative to signal 602, signal 606 has a reduced duty cycle. Whereas signal 602 has a full duty cycle of illumination on times, signal 606 is pulse width modulated at a selected frequency so that light source bank 262 will be energized for only a portion of an illumination on time. Accordingly, the amount of heat radiating from light source bank 262 will be reduced as a result of a change of an applied light source bank driver signal from a setting in accordance with signal 602 to a setting in accordance with signal 606.

Signal 608 represents another embodiment of an energy conserving light source bank driver signal. In one embodiment, apparatus 100 can adjust a light source bank driver signal to exhibit the characteristics shown by signal 608 responsively to a sensed temperature of one or more circuit boards 424, 404, 414, exceeding a threshold. Relative to signal 602, signal 608 has a peak power level of reduced amplitude as well as a reduced duty cycle. Accordingly, the amount of heat radiating from light source bank 262 will be reduced as a result of a change of an applied light source bank driver signal from a signal setting in accordance with signal 602 to a setting in accordance with signal 608.

A technical effect of the hardware and software described herein in certain embodiments is reduced heat absorption in an inspection apparatus. By reducing heat absorption by electrical components of an inspection apparatus, performance and life expectancy of the electrical component can be expected to improve.

A block diagram of an exemplary apparatus capable of supporting the above described processing is shown and described in connection with FIG. 4. Inspection apparatus 100 can include an elongated inspection tube (insertion tube) 112 and a head assembly 114 disposed at a distal end of the elongated inspection tube 112. Inspection apparatus 100 can also include a handset 302 disposed at a proximal end of elongated inspection tube 112.

Regarding head assembly 114, head assembly 114 can include solid state image sensor 132 and imaging optics 140 comprising one or more lenses. Imaging optics 140 can focus an image onto an active surface of solid state image sensor 132. Solid state image sensor 132 can be e.g., a CCD or CMOS image sensor. Solid state image sensor 132 can include a plurality of pixels formed in a plurality of rows and columns. Where solid state image sensor 132 includes a plurality of pixels formed in a plurality of rows and columns, solid state image sensor 132 can be regarded as a two dimensional image sensor. Solid state image sensor 132 can be provided on an integrated circuit. Image sensor 132 can generate image signals in the form of analog voltages representative of light incident on each pixel of the image sensor. Referring to further aspects of head assembly 114, image sensor 132 can be controlled to clock out image signals from image sensor 132. Analog voltages representative of light incident in the various pixels of image sensor 132 can be propagated through signal conditioning circuit 136 along a cable, e.g., a coaxial cable 138 disposed within an elongated inspection tube 112. Head assembly 114 can include signal conditioning circuit 136 which conditions analog image signals for input to cable 138 and receives timing and control signals for control of image sensor 132. Image sensor 132 and signal conditioning circuit 136 can be disposed on a circuit board 139.

Figure 4:
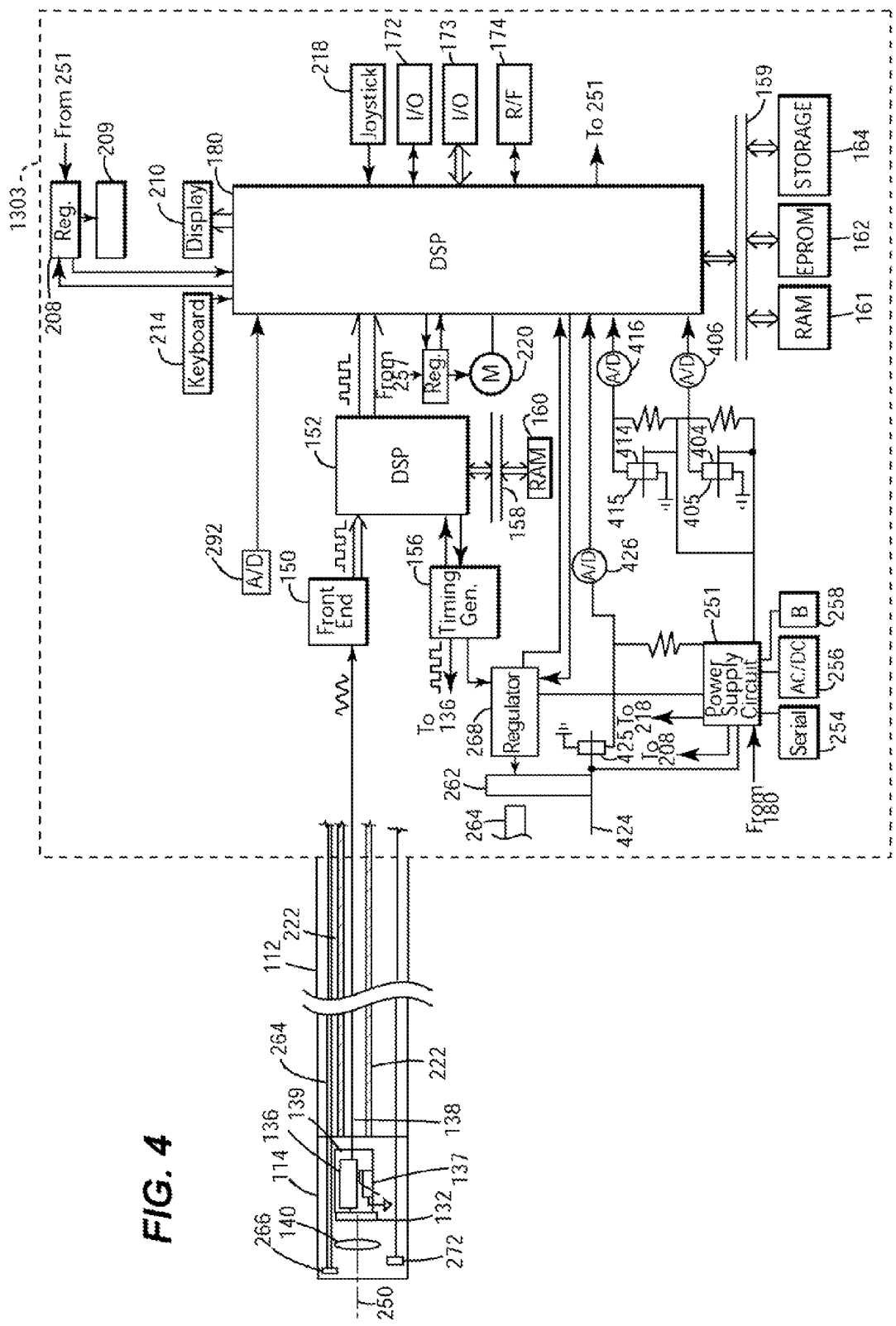
FIG. 4 is a block diagram of an inspection apparatus in one embodiment.

In the embodiment of FIG. 4, a head assembly 114 of apparatus 100 at a distal end of inspection tube 112 comprises image sensor 132. Image sensor 132 of inspection apparatus 100 can, in one alternative embodiment, be located at a position spaced apart from head assembly 114 and disposed at a position rearward of a proximal end of inspection tube 112.

Figure 5:
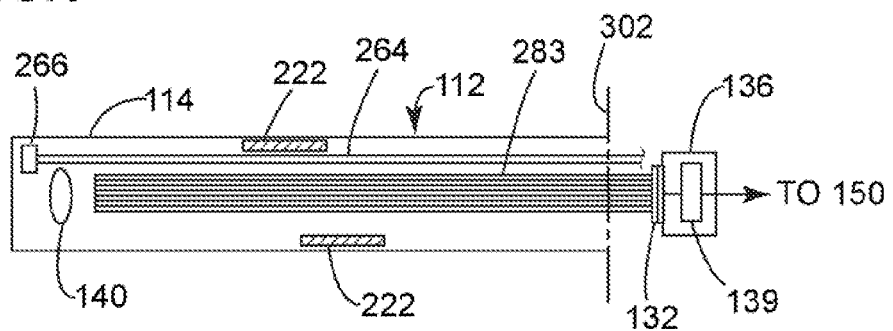
FIG. 5 is a schematic diagram illustrating an alternative embodiment where an image sensor is disposed externally of an inspection tube.

In an alternative embodiment of an inspection apparatus shown in FIG. 5, an imaging system fiber optic bundle 283 can be disposed in inspection tube 112, and can terminate in head assembly 114. The apparatus can be adapted so that such a fiber optic bundle relays image forming light rays from head assembly 114 to the spaced apart image sensor spaced apart from head assembly 114. An example of such an embodiment is illustrated in FIG. 5. In the embodiment of FIG. 5, imaging lens 140 can focus an image of a target 50 onto fiber optic bundle 283, which relays image forming light rays to image sensor 132 which in the embodiment of FIG. 5 is disposed at handset 302 spaced apart from head assembly 114. An inspection apparatus having a fiber optic bundle for relaying image forming light rays is sometimes referred to as a "fiberscope." Inspection apparatus 100 in either of the embodiments of FIG. 4 or FIG. 5 can have an imaging axis 250 extending outwardly from head assembly 114.

Various circuits disposed at a position spaced apart from camera head assembly 114 can receive and process image signals generated by image sensor 132. Such circuits can be regarded as image processing circuitry and can be provided on integrated circuit chips that can be regarded as components of the image processing circuitry. Such components can therefore be regarded as components of processing circuitry 402. Circuits for processing image signals generated by image sensor 132 can be disposed in handset 302. In the exemplary embodiment of FIG. 4, analog front end circuit 150 can include an analog gain circuit, an analog-to-digital converter, and a correlated double sampler and can receive analog image signals, digitize such signals, and transmit digitized image signals to digital signal processor 152 (DSP). DSP 152, in the embodiment shown can be adapted to perform such processing tasks as color matrix processing, gamma processing, and can process digital image signals into a standardized video format, wherein video signals are expressed in a standardized data format. By way of example, video signals output by DSP 152 can be in a BT656 video format and data carried in the video signal can have a 422YCRCB data format. DSP 152 can be in communication with a random access memory 160 through system bus 158. Referring to further aspects of an electrical circuit for inspection apparatus 100, apparatus 100 can include timing generator circuit 156 which can send timing and control signals to signal conditioning circuit 136 for input to image sensor 132 as well as to analog front end circuit 150 and DSP 152. As indicated by communication line labeled "to 136," timing generator circuit 156 can send control signals such as exposure timing signals and frame rate timing signals to circuit 136 for input to image sensor 132. Timing generator circuit 156 can also generate illumination control signals for control of light source bank 262 of apparatus 100. In some embodiments, DSP 152 can be adapted to process image data, and can further be adapted to send imaging parameter (e.g., exposure, illumination) control signals to timing generator 156, which results in timing generator circuit 156 generating imaging circuit 156 generating imaging parameter control signals for input to another component, e.g., circuit 136, or a regulator. In one embodiment, analog circuit front end circuit 150, DSP 152, and timing generator circuit 156 can be provided on separate integrated circuits (ICs). In one embodiment, analog front end circuit 150, DSP 152, and timing generator circuit 156 are provided as part of a commercially available integrated circuit chipset, e.g., an 814612 DSP chipset of the type available from SONY.

Referring to further aspects of apparatus 100, apparatus 100 can include digital signal processor (DSP) 180. DSP 180 can receive the formatted video output from DSP 152 for further processing. DSP 180 can be adapted to perform a variety of image processing tasks such as frame averaging, scaling, zooming, overlaying, merging, image capture, flipping, image enhancement and distortion correction. In one embodiment, DSP 180 can be provided by a TMS32ODM642 Video/Imaging Fixed-Point Digital Signal Processor integrated circuit of the type available from TEXAS INSTRUMENTS. DSP 180 can be in communication with a volatile memory 161, e.g., a RAM, a non-volatile memory 162, and storage memory device 164. Non-volatile memory 162 shown as being provided by an EPROM memory device can also be provided by, e.g., an EEPROM memory device or an EPROM memory device. Software for operating apparatus 100 can be saved in non-volatile memory 162 when apparatus 100 is not operating and loaded into RAM 161 when operation of apparatus 100 is activated. Apparatus 100 can include other types of storage memory. For example, a USB "thumb drive" can be plugged into serial I/O interface 172. A Compact Flash memory card can be plugged into parallel I/O interface 173. A memory of apparatus 100 can be regarded as including memory 160, 161, 162, and 164, other storage memory, as well as internal buffer memories of DSP 152 and 180. Storage memory device 164 can be, e.g., a hard drive or removable disk. RAM 161, non-volatile memory 162, and storage device 164 can be in communication with DSP 180 via system bus 159. While DSP 152 and DSP 180 are shown as being provided on separate integrated circuits, the circuits of DSP 152 and DSP 180 could be provided on a single integrated circuit. Also, the functionalities provided by DSP 152 and DSP 180 could be provided by a general purpose microprocessor IC.

Referring to further circuit components of the block diagram of FIG. 4, apparatus 100 can further include display 210, keyboard 214, and joystick 217, each of which can be interfaced to DSP 180. Display 210, keyboard 214, and joystick 217 form a user interface of apparatus 100 in one embodiment. Keyboard 214 enables a user to initiate various control signals for the control of apparatus 100. Display 210 enables display of live video streaming images and other images to an inspector. For example, apparatus 100 can be controlled to switch from a live streaming video mode in which a live streaming video is being displayed to a mode in which a still image is displayed on display 210. Apparatus 100 can be adapted so that apparatus 100 can generate user-initiated image retention control signals. Apparatus 100 can be adapted so that an inspector can initiate a frame retention control signal by actuating a designated button of keyboard 214. Frame retention control signals can include, e.g., a freeze control signal, and a "take picture" control signal. Apparatus 100 can be adapted so that when a freeze control signal is initiated, apparatus 100 repeatedly reads out to display 210 a frame of image data from a frame buffer. Apparatus 100 can be adapted so that when a "take picture" control signal is initiated, apparatus 100 can save a frame of image data to non-volatile memory 162 and/or storage device 164. Further regarding display 210, apparatus 100 can include a display illuminator 209 for illuminating display 210.

In a further aspect, DSP 180 can be coupled to a serial I/O interface 172, e.g., an ETHERNET, USB interface enabling communication between apparatus 100 and an external computer. DSP 180 can also be coupled to one or more wireless communication interfaces 174, e.g., an IEEE 802.11 wireless transceiver and/or a Bluetooth wireless transceiver. DSP 180 can also be coupled to a parallel I/O interface 173, e.g., a Compact Flash and/or a PCMCIA interface. Apparatus 100 can be adapted to send frames of image data saved in a memory thereof to an external computer and can further be adapted to be responsive to requests for frames of image data saved in a memory device of apparatus 100. Apparatus 100 can incorporate a TCP/IP networking communication protocol stack and can be incorporated in a wide area network including a plurality of local and remote computers, each of the computers also incorporating a TCP/IP networking communication protocol stack.

Referring to further aspects of apparatus 100, apparatus 100 can include joystick 217 for controlling a positioning of head assembly 114. In one embodiment, articulation cables 222 can be incorporated in inspection tube 112 to enable movement of head assembly 114 into a desired position so that a field of view of apparatus 100 can be changed. Joystick 217 can be in communication with DSP 180. Apparatus 100 can be adapted so that control signals for controlling movement (articulation) of head assembly 114 are initiated by manipulating joystick 217. Apparatus 100 can be adapted so that when joystick 217 is moved, DSP 180 receives a control signal from joystick 217 and sends corresponding motor control signals to articulation motor assembly 220 to produce a desired movement of head assembly 114.

In another aspect, inspection apparatus 100 can include a power supply circuit 251. Power supply circuit 251 can be interfaced to various alternative power sources e.g., serial I/O power source 254, AC/DC transformer source 256 and rechargeable battery 258. Apparatus 100 can be adapted to that power supply circuit 251 powers circuit board 404, circuit board 414, and circuit board 424.

Regarding a light source bank 262 of inspection apparatus 100, light source bank 262 of inspection apparatus 100 in one embodiment can be incorporated within housing 303 of handset 302. Bank 262 can include one or more light emitting diodes (LEDs) such as white LEDs. In another embodiment, the one or more light sources of bank 262 can also include one or more laser diode assemblies. LEDs and laser diode assemblies can be regarded as solid state light sources. A fiber optic bundle 264 can be disposed in elongated inspection tube 112 for conducting light from bank 262 through elongated inspection tube 112 and outwardly from head assembly 114 to illuminate a target. A diffuser 266 within head assembly 114 can be provided within head assembly 114 for diffusing light transmitted through fiber optic bundle 264. Light source bank 262 in another embodiment can be provided by one or more arc lamps.

In one aspect as described herein, apparatus 100 can be adapted to control a light source bank driver signal for driving light source bank 262 responsively to a sensing of one or more temperatures of apparatus 100. In one embodiment, thermocouples 425, 405, and 415 can be disposed on each of light source bank circuit board 424, first processing circuit board 404, second processing circuit board 414, respectively, and temperature indicating signals output by thermocouples 425, 405, and 415 can be input into DSP 180, which in turn can responsively generate illumination control signals for input to regulator 268 for controlling light source bank driver signals output by regulator 268. As described hereinabove, apparatus 100 can be adapted to control a light source bank driver signal responsively to sensing a temperature of one or more of circuit boards 424, 404, 414. For inputting a digitized temperature indicating signal output by one of thermocouples 425, 405, 415 a voltage output by a thermocouple 425, 405, 415 can be digitized by a respective analog to digital converter 426, 406, 416, as indicated in the view of FIG. 4.

Figure 6:
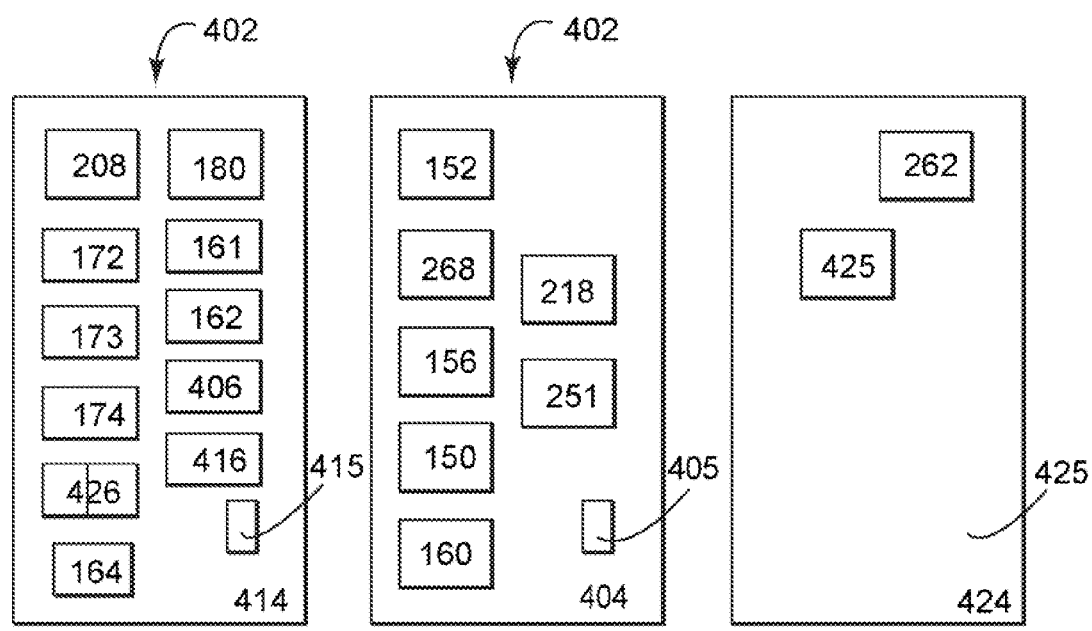
FIG. 6 is a circuit layout diagram illustrating distribution of components of various circuit boards in one embodiment.

Referring to FIG. 6, a circuit board layout drawing in one embodiment is shown and described. As indicated in FIG. 6, light source bank circuit board 424 can carry light source bank 262 and thermocouple 425 and can be regarded as being devoid of processing circuitry 402 (thermocouple 425 can be regarded as a sensor external to processing circuitry 402), circuit board 404 (FIG. 1) can carry electrical components 161, 162, 164, 172, 173, 174, 180, 208, 406, 416, and 426 and circuit board 414 can carry electrical components 150, 152, 156, 160, 218, 251, and 268.

In addition to or as an alternative to presenting energy conserving light source bank driver signals to light source bank 262 responsively to sensed temperature within housing 303, apparatus 100 can present energy conserving illuminator driver signals to display illuminator 209 responsively to sensed temperature and can present energy conserving motor driver signals to motor assembly 220 responsively to sensed temperature within housing 303.

As shown in the block electrical diagram of FIG. 4, display illuminator 209 and motor assembly 220 can have respective regulators 208 and 218 each of which is communicatively coupled to power supply 251. A processor of apparatus 100, such as processor 180 as shown can be adapted to receive inputs from one or more of thermocouples 425, 405, 415 and generate control signals controlling applied power to display illuminator 209 and motor assembly 220 responsively to the output of the one or more thermocouples 425, 405, 415. Such control signals output by the processor can be input to regulator 208 which applies the required driver signal. In the embodiment of FIG. 4, the output of each thermocouple is input to DSP 180.

Figure 7:
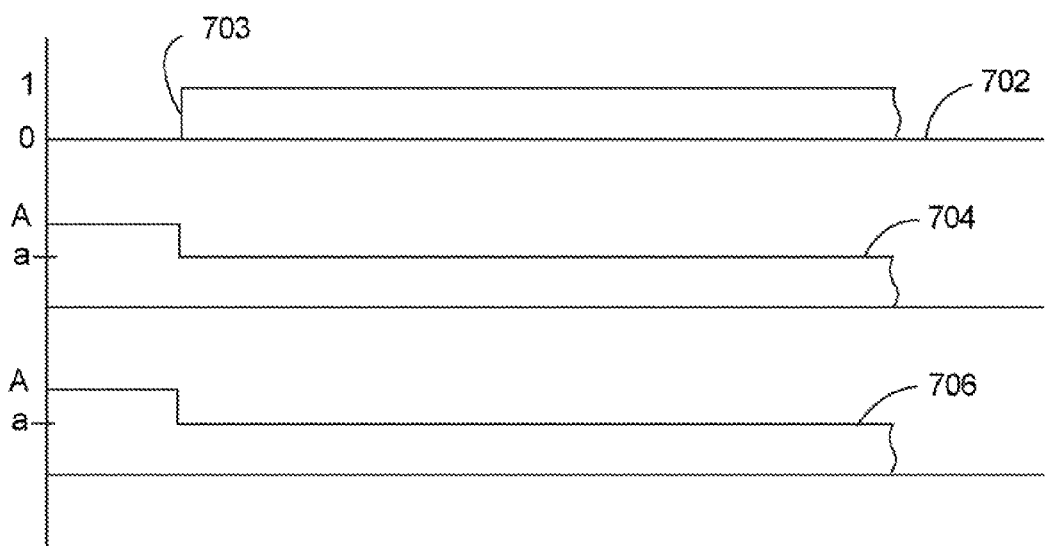
FIG. 7 is a timing diagram illustrating further aspects of a particular thermal control method in one embodiment.

FIG. 7 illustrates applied driver signals applied to display illuminator 209 responsively to sensed temperature, where timeline 702 illustrates a state of a sensed undesirable temperature condition (logic 1 when an undesired temperature is sensed). Signal 704 as shown in FIG. 7 illustrates a driver signal applied to display illuminator 209. Prior to time 703, signal 704 is in accordance with a baseline driver signal and has an amplitude A. After time 703, signal 704 is in accordance with an energy conserving driver signal having reduced amplitude "a" applied to illuminator 209.

FIG. 7 also illustrates applied driver signals applied to motor assembly 220 responsively to sensed temperature. Signal 706 as shown in FIG. 7 is in accordance with a baseline driver signal applied to motor assembly 220 prior to time 703. Signal 706 after time 703 is in accordance with an energy conserving driver signal having amplitude "a" applied to motor assembly 220. In the embodiment described with reference to the timing diagram of FIG. 7, energy conserving driver signals are presented to illuminator 209 and motor assembly 220 simultaneously in response to a sensing of an undesirable temperature at time 703.

It has been mentioned that a different thermocouple 425 may be disposed for sensing a temperature of light source bank 262 and its associated circuit board that is disposed for sensing a temperature of a processing circuit board such as board 404 and its associated circuitry. With separate temperature sensors deployed, a thermal control system can be provided which can accordingly sense temperatures at different locations within hand held housing 303. Spaced apart electrical components within housing 303 may exhibit significantly different temperatures where the components are advantageously thermally separated as will be explained herein or where the components are in thermal communication but there is appreciable time delay for heat to conduct from one component to another.

The inventors discovered that the power consumption and associated heat generating characteristics of light source bank 262 processing components including image processing components are not always similar. That is, in some instances it may be desirable to employ a light source bank having higher power consumption and heat generating ratings than processing circuitry components. In some instances it may be desirable to employ processing circuitry components having higher power consumption and heat generating ratings than light source bank electrical components. It will be seen that such selections can be achievable by deployment of a heat sink assembly having thermally separated heat sink paths. A thermal control system as described having multiple temperature sensors can provide accurate sensing of temperatures at various locations within housing 303 even where components within housing 303 are provided on separate heat sinking paths.

A high wattage and significant heat generating light source bank 262 can be disposed in apparatus 100 having higher wattage and heat generating ratings than associated processing circuitry 402 by thermally separating the light source bank from the processing circuitry 402 and by providing a thermal control system having a thermocouple 425 for sensing a temperature of light source bank 262 and a different thermocouple e.g., thermocouple 405 or 415 for sensing a temperature of processing circuitry 402 of apparatus 100.

A thermal control system which initiates a cooling procedure responsively to a sensed temperature can be adapted so that cooling procedure is responsive to a temperature sensed by the thermocouple 425 exceeding a first threshold temperature and of thermocouple 405 or 415 exceeding a second threshold temperature lower than the first threshold temperature (higher temperatures in the area of light source bank being tolerated). As indicated, a cooling procedure can comprise presenting energy conserving driver signals to one or more of light source bank 262, display illuminator 209 and articulation cable motor assembly 220.

In another aspect a heat sink assembly can be incorporated in the apparatus having separate heat sink paths for conducting heat from each of a first location and a second location within hand held housing 303. In one embodiment, a first set of heat sink members can be deployed to conduct heat from the first location and a second set of one or more heat sink members can be employed to conduct heat from the second location and further the first set and the second set can be maintained in thermal separated. Regarding "thermal separation" described herein, it should be noted that heat may be transferred between two thermally separated components by way of convection given that a pair of components can be commonly disposed in a single compact housing 303. Nevertheless, a pair of electrical components can be regarded as thermally separated where the apparatus is devoid of a thermally conductive path comprising one or more heat sink members between the components.

Aspects of a heat sink assembly for apparatus 100 in one embodiment are now further described. Various aspects of apparatus 100 in one embodiment are described with reference to the exploded view of FIG. 1 and FIGS. 8-12.

Figure 8:
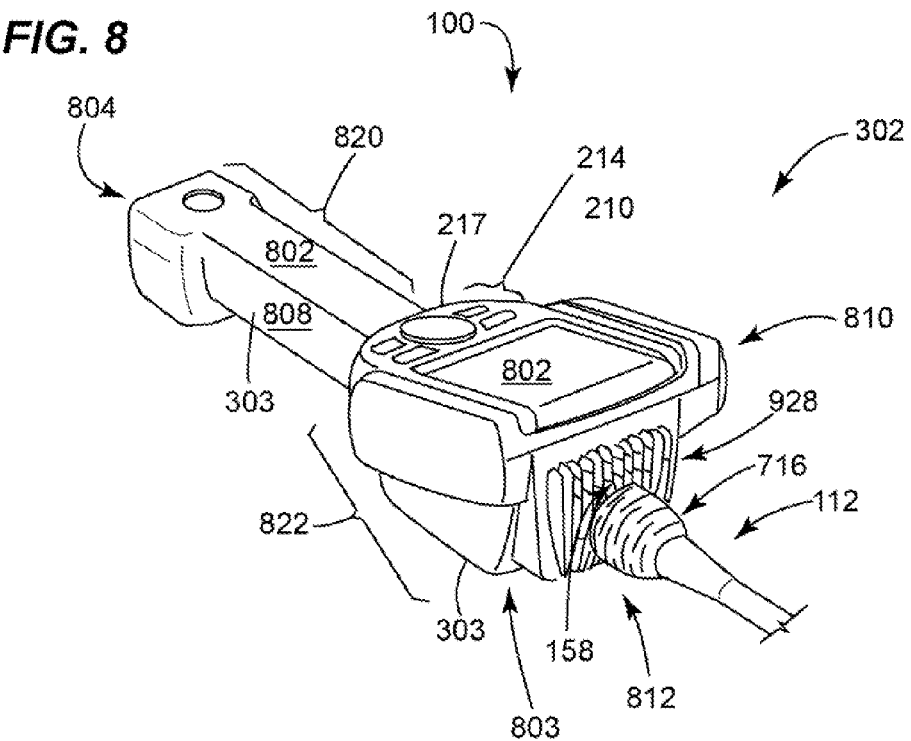
FIG. 8 is a physical form perspective view of a visual inspection apparatus having a heat sink assembly.

It is seen that handset 302 having hand held housing 303 can include a top 802, a rear 804, a bottom 806, a pair of sides 808 and 810, and a front 812. On top 802 there is disposed a display 210, keyboard 214 and joystick 217. In the particular embodiment of FIGS. 1 and 8-12, a handle 820 defining rear 804 extends rearward from major body 822 of handset 302. In use, an inspector can grasp handset 302 primarily at handle 820, but at times may stabilize handset 302 by further holding of handset at bottom 806 and sides 808, 810. Apparatus 100 as noted also includes elongated inspection tube 112 that among other functions transmits illumination light rays generated by light source bank 262 for illumination of a target substrate 50. In one embodiment, apparatus 100 as shown in FIG. 8 where the components are shown in true relative scale can have the approximate dimensions of 30 cm length, 15 cm maximum width, and 15 cm maximum height.

Referring to aspects of a heat sink assembly of apparatus 100 in further detail, a heat sink assembly of apparatus 100 can have exposed sections of heat sink members facing forwardly from a front of handset 302 and in the embodiment shown is devoid of heat sink members facing outwardly from a top, bottom, sides, or rear of handset 302. In such manner, the members of the described heat sink assembly are confined to locations that are unlikely to be contacted by an inspector in use while an inspector holds and stabilizes the handset during performing an inspection. While in the embodiment shown, the described heat sink assembly advantageously is devoid of exposed heat sink members facing outwardly from a side, bottom, top, or rear of handset 302 in some embodiments it is envisioned that disposing heat sink components at such positions can be advantageous.

In another aspect the heat sink assembly incorporates heat sink member components that serve a function other than heat sinking. The heat sink assembly in the embodiment of FIGS. 1 and 8-12 can incorporate components of elongated inspection tube 112 which like the remaining components of the heat sink assembly in the embodiment of FIGS. 1 and 8-12 can extend forwardly from a major body 822 of handset 302 and from housing 303.

A function of a heat sink assembly of apparatus 100 is to draw heat away from internal components internal to hand held housing 303. In a visual inspection apparatus there can be deployed an elongated inspection tube 112, and such an elongated inspection tube can extend externally from a handset of the apparatus. In the heat sink assembly as shown in FIGS. 1 and 8-12, components of elongated inspection tube 112 can be employed as heat sink components for removing heat from internal electrical components disposed within hand held housing 302. In such manner additional cost which would ensue by incorporating additional dedicated heat sink members is avoided, and the size and weight of apparatus 100 is reduced. In the embodiment shown, connecting flange 908, monocoil 912, and nut 916 which are components of elongated inspection tube 112 are deployed as heat sink members.

In another aspect a heat sink assembly of apparatus 100 can include a first set of heat sink members for drawing heat away from one or more electrical components at a first location within hand held housing 303 and a second set of heat sink members for drawing heat away from one or more electrical components at a second location within hand held housing 303. Each of the first set and the set of heat sink members can include one or more members, and each of the first and second set of heat sink members can be in thermal separation with respect to one another. Each of the heat sink members described herein as a heat sink member can be a single piece member. Further, each component described as a heat sink member comprises thermally conductive material.

Figure 9:
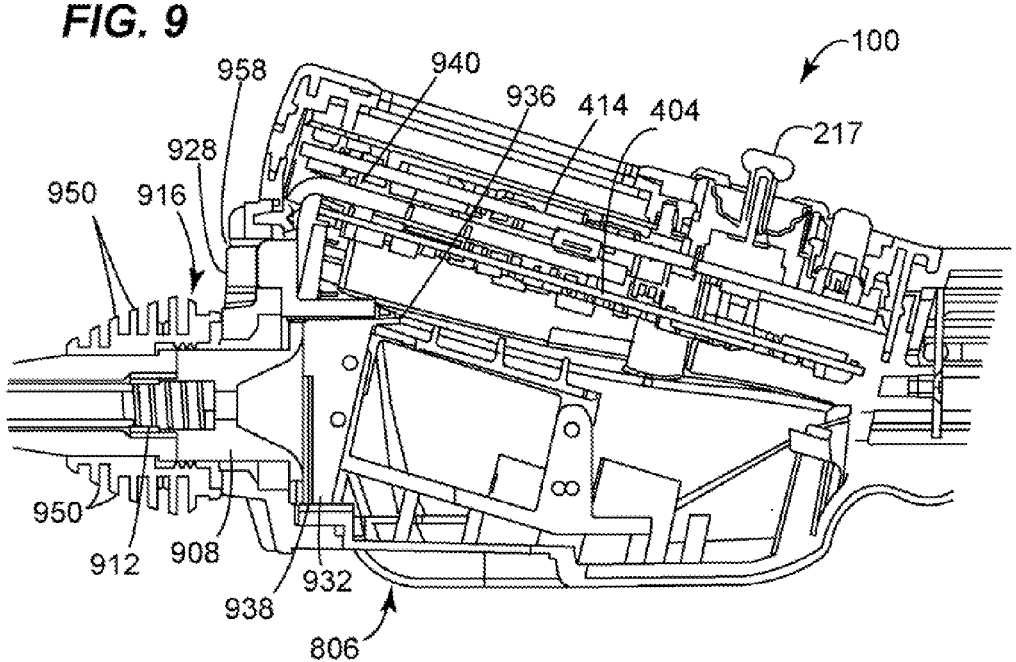
FIG. 9 is a cutaway side view of a visual inspection apparatus having a heat sink assembly.
Figure 10:
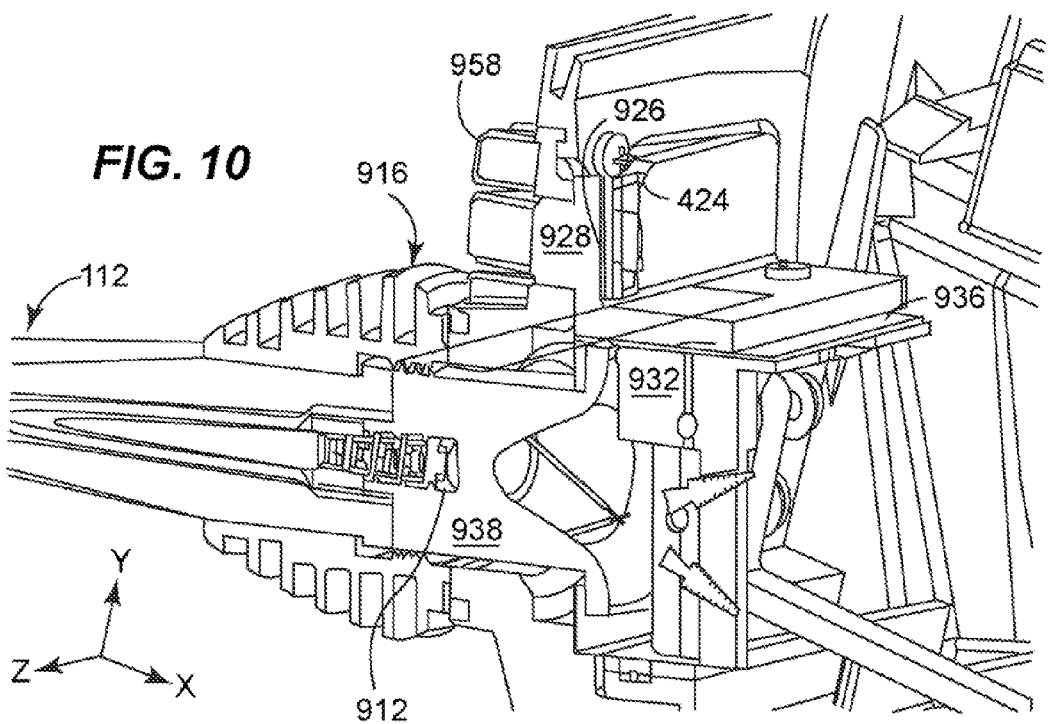
FIG. 10 is an exploded cutaway perspective side view of a visual inspection apparatus having a heat sink assembly.
Figure 11:
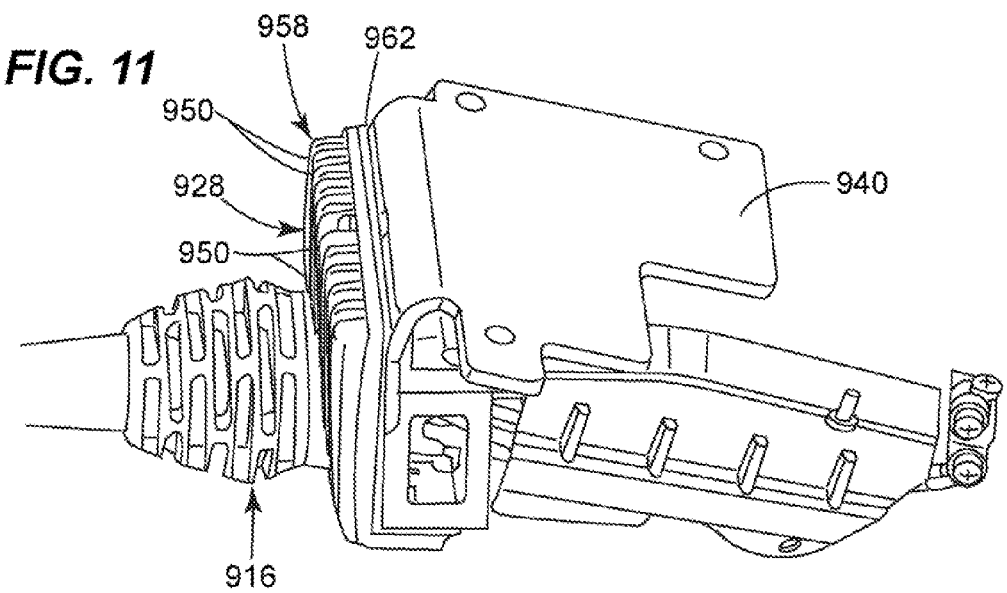
FIG. 11 is a perspective partial view of the visual inspection apparatus as shown in FIG. 10 illustrating a heat spreader heat sink member.

Elements of such first and second sets of heat sink members are described with reference to the illustrative embodiment of FIGS. 1 and 8-12. With further reference to the views of FIGS. 1 and 8-12, light source bank circuit board 424 carrying light source bank 262 can be mounted to multi-finned heat sink member 928 which has a portion facing an exterior of housing 303 which also extends forward from a major body of handset 302 and from housing 303 and has fins 950 exposed to an exterior of housing 303. Thermal pad 926 can be interposed between light source bank circuit board 424 and multi-finned heat sink member 928 for increasing thermal conduction between heat sink members 424 and 928. As best seen in FIG. 9, multi-finned heat sink member 928 can in turn be thermally connected to a heat sink member in the form insertion tube flange 908. Multi-finned heat sink member 928 can also be thermally connected to interface member 932 serving as a heat sink member. For providing thermal communication between heat sink members e.g., member 928 and 932, the members may be placed in contact with one another. However, for increasing thermal communication between two rigid e.g., metal members a deformable thermal pad can be interposed between the two members. Such a thermal pad can comprise a thermally conductive elastomer.

It has been described that thermal pad 926 can be interposed between heat sink members 424 and 928. As best seen in FIG. 9, thermal pad 936 serving as a heat sink member can be interposed between interface 932 and multi-finned heat sink member 928 and between multi-finned heat sink member 928 and flange 908. Referring to further aspects of the heat sink assembly of the exemplary embodiment described, flange 908 can be in thermal communication with interface 932 via pad 938 interposed between flange 908 and interface 932.

Referring to further aspects of a heat sink assembly of an exemplary embodiment, the heat sink member provided by flange 908 can be metallic and thermally conductive and can extend forwardly away from major body 822 and from housing 303 for removal of heat energy from one or more internal electrical components, e.g., light source bank 262 internal to housing 303. In a further aspect, flange 908 can be in thermal communication with monocoil 912. Monocoil 912 can be provided as part of insertion tube 112, and can be provided by an elongated helical metal structure that is disposed about an axis of the insertion tube and can extend forwardly along a length of insertion tube toward a distal end of the insertion tube. One function of monocoil 912 is to provide crush resistance for insertion tube 112. Insertion tube 112 can house an array of sensitive and costly components, e.g., articulation cables one or more fiber optic bundles and electrical conductors. Accordingly, including monocoil 912 for crush resistance provides an important function.

In another aspect deployed as described in FIG. 9, monocoil 912 also serves as a heat sink member of a heat sink assembly. For thermal communication between thermally conducting flange 908 and monocoil 912, monocoil 912 and flange 908 can be soldered together with use of a thermally conductive solder material which serves as a heat sink member.

In another aspect of the heat sink assembly of the particular embodiment described, a cover nut 916 of insertion tube 112 shown extending forwardly of major body 822 and housing 303 can serve as a heat sink member of heat sink assembly 900. In one operational aspect, nut 916 operates to secure insertion tube 112 to handset 302. Specifically an internal portion of nut 916 can be threaded and can be adapted to threadably engage threads of flange 908. Apparatus 100 can be adapted so that threading of nut 916 onto flange 908 presses flange 908 toward major body 822 causing secure connection between insertion tube 112 and the major body 822. In another operational aspect of cover nut 916, cover nut 916 serves as a heat sink member. Cover nut 916 can be formed to be thermally conductive so that contacting of nut 916 to flange 908 helps to further draw heat energy way from an interior of housing 303. Thermal contact between flange 908 and nut 916 can be provided by the mating threads between the two heat sink components. It will be seen that components of an elongated inspection tube can be adapted for heat sinking where the inspection apparatus is other than a visual inspection apparatus. Eddy current sensors and ultrasonic sensors also have elongated insertion tubes. In another variation, components of such tubes can be adapted for heat sinking of handset internally disposed one or more electrical component as described herein.

In another aspect, thermally conductive cover nut 916 can be formed to be multi-finned as shown e.g., in FIG. 9 for increasing the surface area thereof and accordingly for increasing the amount of heat radiation that is removed by cover nut. Cover nut 916 can include multiple fins 950 facing an exterior of handset 302.

Referring to still further aspects of the heat sink assembly 900 described, the above set of heat sink members for drawing heat away from a light source bank 262 at a first location can be provided in combination with a second set of heat sink members thermally separate from the first set of heat sink members. A description of a second set of heat sink members for drawing heat away from components at a second location within housing 303 will now be described.

As seen in the views of FIGS. 1 and 8-12, a heat spreader 940 in the specific embodiment described can be interposed between circuit board 404 and circuit board 414. For increasing thermal communication between electrical component of circuit board 404 and circuit board 414 respective thermal pads (not shown) can be affixed to both a top surface and a bottom surface of heat spreader 940. When circuit board 404, heat spreader 940, and circuit board 414 are installed, the noted components can be arranged so that the noted thermal pads contacting the top and bottom of heat spreader 940 abut integrated circuit chips of board 404 and board 414 to increase the thermal communication between the processing circuitry provided by the chips to heat spreader 940.

In another aspect of the heat sink assembly described in various views, the heat sink member provided by spreader 940 can be provided in thermal contact with multi-finned heat sink member 958 which like multi-finned heat sink member 928 extends forwardly from a major body of handset and from housing 303 and faces an exterior of housing 303. For thermal communication between spreader 940 and multi-finned heat sink member 958, a thermal pad 962 can be interposed between spreader 940 and multi-finned heat sink member.

A heat sink assembly as described herein with reference to the various views can be regarded to include thermally conductive components 928, 424, 936, 932, 916, 404, 940, 414, 938, 912, 908, 958.

Figure 12:
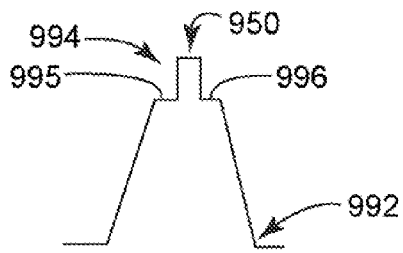
FIG. 12 is a cutaway side view of a heat sink fin.

It has been noted that one or more heat sink members of the heat sink assembly (e.g., member 916, 928, 958) described herein can include multiple fins 950. A possible construction of such fins is described with reference to FIG. 12, showing a cross sectional view of a fin that can be part of a set of fins. The incorporation of fins 950 into a heat sink member increases the surface area of the heat sink member, and therefore the exposure of the heat sink member to cooler temperatures, where the fins are exposed to an exterior of housing 303.

According to the cross sectional view of FIG. 12, it is seen that a fin 950 can be characterized by a narrowing thickness from base 992 to tip 994. By providing a tip 994 having a thickness that is relatively narrow as compared to a fin base 992, a temperature gradient can be created allowing a tip to be relatively cooler than base 992. A reduced thickness at a tip 994 inhibits the flow of heat along the tip 994, allowing the tip to be cooler than a remainder of a fin 950.

While tapering of a fin from bottom to tip 994 can result in a tip being cooler than the lower portions of the fin 950, a particularly desirable temperature gradient and one that results in a fin that is particularly comfortable to the touch can be achieved with the configuration as shown in FIG. 12 including at least one step such as may be provided by step 995 and step 996 for providing a step-wise reduction in the fin thickness at the tip of the fin 950. In the particular embodiment of FIG. 12, fin 950 has a generally tapered major cross sectional body and a tip 994 having a stepwise reduced thickness relative to a remainder of fin 950.

It has been described that in one embodiment, apparatus 100 can be adapted so that heat a sink assembly of apparatus 100 has exposed members at such locations as to reduce the likelihood of such a contact by an inspector during use. Nevertheless, fins 950 of a multi-finned heat sink member (e.g., member 916, 928, 958) with reduced thickness from base to tip, renders the multi-finned heat sink members more comfortable to the touch in the event they do happen to be contacted by an inspector during use. Making fins comfortable to the touch is particularly advantageous where contact of a heat sink member is required during or just after an inspection. For example, multi-finned cover nut may be contacted during or between inspections to allow for removal and replacement of an insertion tube or another type of inspection probe.

With reference to FIGS. 1, 8-12 it has been described that while multi-finned heat sink member 928 and multi-finned heat sink member 958 can be provided as members of thermally separated thermally conductive paths, the members 928, 958 can be in close proximity of one another. For insuring thermal separation between heat sink member 928 and heat sink member 958 thermally insulating material can be interposed in the interface between the members. In another aspect, heat sink member 958 can be peripherally disposed about heat sink member 928 as shown. Such a configuration reduces the likelihood that an inspector will contact heat sink member 928. The arrangement where heat sink member 958 is peripherally disposed about heat sink member 958 can be advantageous where heat sink member 928 is expected to exhibit significantly higher temperatures than peripherally disposed heat sink member 928. Where heat sink member 928 is in communication with a relatively high wattage light source bank 262, heat sink member 928 might exhibit significantly higher temperatures than heat sink member 958. While the arrangement shown where heat sink member 958 is peripherally disposed about heat sink member 928 360 degrees, other arrangements e.g., where member 958 is peripherally disposed 180 degrees or 270 degrees about member 928 will also be useful in discouraging contact between a heat sink member 928 and an inspector.

As has been mentioned, thermal separation between heat sink paths of apparatus 100 can facilitate selection of a high wattage light source bank 262 capable of tolerating heat which if conducted to processing components of apparatus 100 (e.g., image processing components) might negatively impact the operation of such components. An illustrative embodiment is described in Table A, illustrating exemplary average power consumption ratings of circuit boards 424 of apparatus 100. In Table A an embodiment is described having a relatively high wattage light source bank 262.

TABLE A

| Power Rating 424 | 9 W |
| Power Rating 404 | 4 W |
| Power Rating 414 | 4 W |
| Threshold 425 | 90° C. |
| Threshold 405 | 80° C. |
| Threshold 415 | 85° C. |

In the embodiment of Table A, printed circuit board 404 and printed circuit board 414 have average power consumption ratings of about 4 W and light source bank circuit board 424 has an average power consumption rating of about 9 W. In the described embodiment, thermal separation of a heat sink path for light source bank 262 can yield important advantages; as the separation can protect and prevent thermal damage and degradation to the components of circuit board 404 and circuit board 414.

Also referring to Table A, it is seen that cooling procedure thresholds can vary for each thermocouple 425, 404, 414. Where light source bank 262 is of relatively high wattage and the heat sink capacity for the light source bank 262 and the thermally separated processing circuitry 402 is on the same order of magnitude it can be expected that a threshold for thermocouple 425 will generally be higher than for either thermocouple 405 or thermocouple 415.

It has been described that apparatus 100 can utilize more than one different threshold for determining whether to initiate a cooling procedure. For example, apparatus 100 may compare an output of thermocouple 425 to a first threshold and may compare an output of thermocouple 405 to a second threshold for determining whether a cooling procedure should be initiated.

In another aspect, a threshold for use in determining whether a cooling procedure should be initiated can be determined based on a temperature of an exposed heat sink assembly member e.g., member 428, 458. It has been described that exposed heat sink members such as heat sink member 428 and heat sink member 458 that are exposed to an exterior of housing 303 can be particularly positioned so as to reduce of incidence of contact between an inspector and the heat sink member. In another aspect a temperature of an exposed heat sink member such as heat sink member 428, 458 can be monitored and regulated to assure that a temperature of the exposed heat sink member does not exceed a temperature that could pose a health risk to an inspector. The inventors determined that a temperature exhibited by an exposed heat sink member of apparatus of above 70° C. would pose an unacceptable health risk to inspectors.

For assuring that a temperature of an exposed heat sink member does not exceed a determined temperature apparatus 100 can be adapted so that apparatus 100 senses a temperature of heat sink member 428 and responsively to the sensed temperature can initiate one or more of the described cooling procedures to cool an interior of hand held housing 303. Further, the inventors determined that temperature sensed by a temperature sensor e.g., within housing 303, serves as surrogate measure of a temperature of heat sink member 428 provided the temperature sensor is in thermal communication with the heat sink member 428.

In the embodiment described herein wherein heat sink member 428 is in thermal communication with light source bank circuit board 424 a temperature of heat sink member 428 can be sensed by a thermal sensor such as thermocouple 455 disposed at circuit board 424. In a setup mode sensor output temperatures corresponding to exposed heat sink member sections can be empirically determined by recording sensor output values of sensor 425 that are correlated with actual measure heat sink member temperatures. In one embodiment a temperature of 90° C. sensed by thermocouple 425 (which is used as the light source circuit board threshold temperature in the example of Table A) translates to a temperature of 70° C. at an exposed section of heat sink member 428.

In another embodiment, where an average power consumption rating of light source bank 262 is relatively lower, e.g., it might be advantageous to thermally connect the two thermally separate heat sink paths described hereinabove. For thermal connection between the described heat sink paths thermally insulating material between heat sink member 428 and heat sink member 458 can be replaced with thermally conductive material.

Accordingly apparatus 100 facilitates simple reconfiguration in the case it is desired to switch out and exchange a light source bank 262 to a new light source bank having a different power consumption rating.

Referring to the thermal control flow diagram of FIG. 2, it has been described that the cooling procedure indicated by block 506 can be supplemented or replaced by alternative cooling procedures wherein energy conserving driver signals are presented to alternative electrical components e.g., motor assembly 220 or illuminator 209.

In the embodiment described with reference to FIG. 13 apparatus 100 can be adapted so that responsively to sensing a temperature above a threshold apparatus 100 can initiate additional cooling procedures in sequence after expiration of various timeout periods. Referring to the timing diagram of FIG. 13 where timeline 1304 illustrates an activation state of a first cooling procedure, timeline 1306 illustrates an activation state of a second cooling procedure and timeline 1308 illustrates an activation state of the third cooling procedure, timeline 1302 can indicate a time at which a sensed temperature remains above a threshold.

Figure 13:
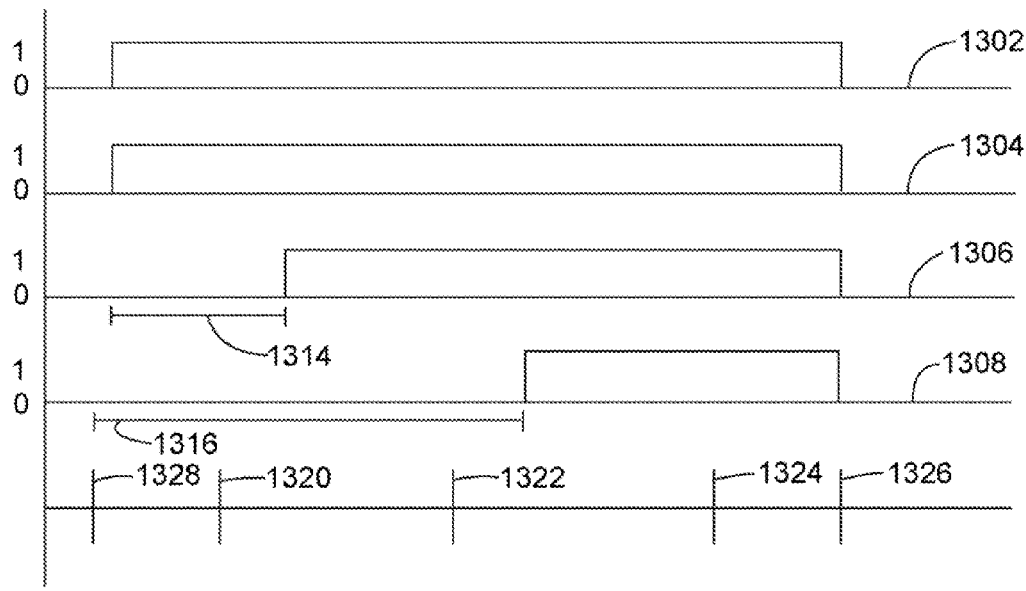
FIG. 13 is a timing diagram illustrating further aspects of a particular thermal control method in one embodiment.

Referring to the timing diagram of FIG. 13 it is seen that apparatus 100 can be adapted to maintain a first cooling procedure in an active state for an entire time an undesirable temperature conduction is sensed, and if an undesirable temperature conduction remains sensed for timeout period 1314 apparatus 100 can activate a second cooling procedure. Further, if apparatus 100 senses an undesirable temperature condition for a second timeout period 1316 apparatus can activate a third cooling procedure the activation state of which is represented by timeline 1306. Once a high temperature condition is determined to be alleviated at time 1326 each of the activated cooling procedures can be deactivated simultaneously. At time 1320 apparatus 100 can run a single cooling procedure. At time 1322 apparatus 100 can simultaneously run two cooling procedures. At time 1324 apparatus 100 can simultaneously run three cooling procedures.

The described timed sequenced initiation of cooling procedures provides cooling with reduced impact on the featurization of the apparatus 100. In another aspect an inspection apparatus can be adapted so that an inspector can select an ordering of initiation of cooling procedures. For example, in a default mode apparatus 100 may be set up to initiate a power reduced light source bank cooling procedure first, then a reduced power motor assembly procedure, then a reduced power illuminator procedure. However, an inspector performing an inspection where maximum powered target illumination would be beneficial might wish to alter the ordering of the noted cooling procedures.

Figure 14:
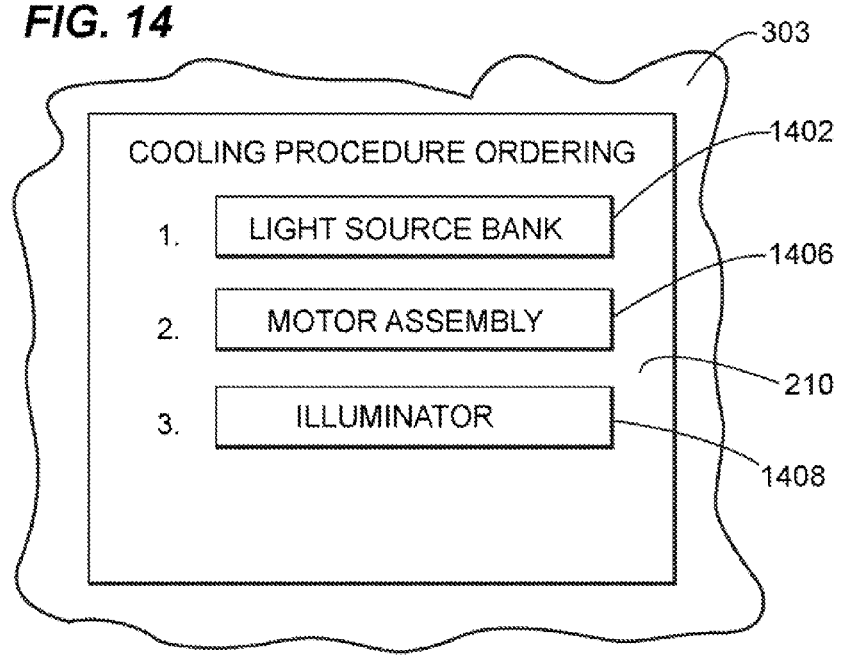
FIG. 14 is a top view of an inspection apparatus having a user interface allowing an inspection user to select a priority of sequenced cooling procedures.

In one embodiment as described in FIG. 14, an inspector can be presented with a menu screen on display 210, showing a presently established ordering of timed sequenced cooling procedures. Apparatus 100 can be adapted so that an inspector can change the presently established ordering of the procedures by dragging and dropping the button 1402, 1406, or 1408 corresponding to the desired procedure in the desired procedure sequence.

Still further, apparatus 100 can be adapted so that an inspector can disable a cooling procedure in such manner that a cooling procedure selected for disabling will not be performed even if an undesirable temperature is sensed within apparatus 100. For example, if an inspector wishes to perform an inspection where full range of movement of inspection tube 112 is desired an inspector may wish to disable the cooling procedure. Accordingly, apparatus 100 can be adapted so that action taken by an inspector user using a user interface of apparatus 100 will disable a procedure. For example, apparatus 100 can be adapted so that double clicking a button 1402, 1406, or 1408 will disable the cooling procedure corresponding to the button.

In another aspect apparatus 100 can be adapted to carry out a power supply shut down. It has been described that apparatus 100 can have disposed internal of housing 303 a power supply circuit 251 which is sourced by a battery 258 also disposed within hand held housing 303. In one embodiment, apparatus 100 can be adapted to execute a shutdown responsively to a monitoring of a success of a cooling procedure. For example, apparatus 100 can be adapted to monitor an output of one or more of the apparatus temperature sensors at timed intervals e.g., at times 1320, 1322, 1324 after sensing an undesirable temperature at time 1318. If according to a criteria the one or more active cooling procedures are not providing a desired cooling effect (e.g., if cooling is not progressing at a fast enough rate or if temperature is actually increasing) apparatus 100 can initiate a shut down procedure.

As part of a shutdown procedure, apparatus 100 can transfer any data currently retained in volatile memory 160, 161 into non-volatile memory 162, 164. Also as part of a cooling procedure apparatus 100 can transmit data from one or more memories 160, 161, 162, 164 to an external computer in communication with but spaced apart from apparatus 100. For example, apparatus 100 can transmit data currently stored in memory 160, 161, 162, 164 over a communication interface device e.g., interface 172, interface 173, or interface 174 to an external computer. Also as part of a shutdown procedure after the data store and data transmission steps are complete apparatus 100 can shut down power supply circuit 251. For example, DSP 180 can send a control signal to power supply circuit 251 and power supply circuit 251 can responsively cut off power to the various electrical components of apparatus 100.

In another aspect, handset 302 can be adapted in one embodiment to be liquid tight in such manner that liquid is prevented from entering an interior of housing 303. When handset 302 is adapted to be liquid tight, handset 302 can be devoid of a fan for cooling internal components as handset 302 will be devoid of a fluid outlet opening. In such an embodiment, the cooling effected by a thermal control system and a heat sink assembly as described herein are particularly advantageous.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A visual inspection apparatus for use in inspecting an industrial equipment article defining a target substrate, said visual inspection apparatus comprising:
   a two dimensional image sensor and imaging optics for focusing images of said target substrate onto said two dimensional image sensor;
   image processing circuitry for processing image signals representative of light incident on said two dimensional image sensor;
   at least one processing circuit board carrying at least one component of said image processing circuitry;
   a light source bank for illuminating a target substrate;
   at least one temperature sensor;
   a display for displaying image representations corresponding to light incident on said two dimensional image sensor;
   a hand held housing encapsulating said at least one processing circuit board and said light source bank and said at least one temperature sensor, said hand held housing having disposed thereon said display; and
   an elongated inspection tube adapted to transmit light generated by said light source bank so that said light generated by said light source bank can be directed to said target substrate, said elongated inspection tube extending front said hand held housing,
   wherein said visual inspection apparatus is adapted so that said visual inspection apparatus can initiate a first cooling procedure and a second cooling procedure for cooling an interior of said hand held housing responsively to a temperature sensed by said at least one temperature sensor,
   wherein the first cooling procedure and the second cooling procedure modify operation of different components on said visual inspection apparatus, and
   wherein said visual inspection apparatus initiates said first cooling procedure and said second cooling procedure in accordance with a timed sequence comprising one or more time periods that define a time the sensed temperature exceeds a threshold value, the time periods comprising a first time period during which said first cooling procedure is active and a second time period during which said second cooling procedure is active.

2. The visual inspection apparatus of claim 1, wherein said visual inspection apparatus includes an articulation motor assembly for moving said elongated, inspection tube responsively to user input control and an illuminator for backlighting said display, and wherein at least one of said first cooling procedure and said second cooling procedure includes at least one of presenting an energy conserving light source bank driver signal to said light source bank, presenting an energy conserving motor assembly driver signal to a motor assembly of said visual inspection apparatus, and presenting an energy conserving illuminator driver signal to said illuminator.

3. The visual inspection apparatus of claim 1, wherein said visual inspection apparatus includes an articulation motor assembly for moving said elongated inspection tube responsively to user input control and an illuminator for backlighting said display, wherein said first cooling procedure and said second cooling procedure are selected from the group consisting of presenting an energy conserving light source bank driver signal to said light source bank, presenting an energy conserving motor assembly driver signal to a motor assembly of said visual inspection apparatus, and presenting an energy conserving illuminator driver signal to said illuminator, and wherein said at least two cooling procedures are carried out in sequence after an undesirable temperature is sensed.

4. The visual inspection apparatus of claim 3, wherein said visual inspection apparatus is adapted so that said at least two cooling procedures are carried out in sequence according to an established priority.

5. The visual inspection apparatus of claim 3, wherein said visual inspection apparatus includes a user interface and is adapted so that said at least two procedures are carried out according to an established priority, and wherein said visual inspection apparatus is adapted so that a user of said visual inspection apparatus can select, using said user interface, an order of said established priority.

6. The visual inspection apparatus of claim 1, wherein said visual inspection apparatus includes an articulation motor assembly for moving said elongated inspection tube responsively to user input control and an illuminator for backlighting said display, wherein said first cooling procedure and said second cooling procedure are selected from the group consisting of presenting an energy conserving light source bank driver signal to said light source bank, presenting an energy conserving motor assembly driver signal to a motor assembly of said visual inspection apparatus, and presenting an energy conserving illuminator driver signal to said illuminator, wherein said visual inspection apparatus includes a user interface, and wherein said visual inspection apparatus is adapted so that a user of said visual inspection apparatus with use said user interface to disable at least one of said first cooling procedure and said second cooling procedure to prevent execution ring operation of said visual inspection apparatus even if an undesirable temperature is sensed.

7. The visual inspection apparatus of claim 1, wherein said visual inspection apparatus has an internal power supply internally disposed within said hand held housing, said power supply being in communication with a battery power source that is also disposed within said hand held housing, wherein said visual inspection apparatus is adapted to monitor a success of said first cooling procedure and second cooling procedure at a time after initiation, the success indicated by a change in the sensed temperature as compared to the threshold value, and wherein said visual inspection apparatus further in response to said monitoring can execute a shutdown procedure characterized by at least one of (a) saving data retained in volatile memory into a nonvolatile memory internal to the handheld housing, (b) transmitting data to an external computer, and (c) shutting off said power supply.

8. The visual inspection apparatus of claim 1, wherein at least one of said first cooling procedure and said second cooling procedure includes presenting an energy conserving light source bank driver signal to said light source bank, said energy conserving light source bank driver signal having a reduced duty cycle relative to a baseline light source bank driver signal.

9. The visual inspection apparatus of claim 1, wherein at least one of said first cooling procedure and said second cooling procedure includes presenting an energy conserving light source bank driver signal to said light source bank.

10. The visual inspection apparatus of claim 1, wherein said light source bank is thermally separated from said at least one processing circuit board.

11. The visual inspection apparatus of claim 1, wherein said apparatus is adapted so that said light source hank is thermally separated from each processing circuitry component of said apparatus.

12. A visual inspection apparatus, comprising:
a handset including at least a display and a keyboard and being delimited by a hand held housing;
a two dimensional image sensor and associated optics for focusing an image of said target substrate onto said two dimensional image sensor;
a light source bank for illuminating said target substrate;
processing circuitry including image processing circuitry for processing image data representing light incident on said two dimensional image sensor, wherein both of said light source bank and said processing circuitry are disposed within said hand held housing, and wherein said visual inspection apparatus is adapted so that there can be displayed on said display image data representing light incident on said two dimensional image sensor;
an elongated inspection tube extending from said handset and being adapted to transmit light generated by said light source bank for illumination of said target substrate;
wherein said visual inspection apparatus is adapted so that said light source bank and components of said processing circuitry are maintained in thermal separation, said visual inspection apparatus being devoid of a material thermally conductive path between said light source bank and said components of said processing circuitry;
a first thermal sensor for sensing a temperature of said light source bank; and
a second thermal sensor for sensing a temperature of said processing circuitry;
wherein said visual inspection apparatus is adapted to initiate at least one cooling procedure responsively to a sensed temperature indicating output of at least one of said first thermal sensor and said second thermal sensor,
wherein said visual inspection apparatus includes an articulation motor assembly for moving said elongated inspection tube responsively to user input control,
wherein said at least one cooling procedure includes at least two cooling procedures selected from the group consisting of (a) presenting an energy conserving light source bank driver signal to said light source bank, (b) presenting an energy conserving motor assembly driver signal to a motor assembly of said visual inspection apparatus, and (c) presenting an energy conserving illuminator driver signal to said illuminator, and
wherein said visual inspection apparatus is further adapted so that said visual inspection apparatus can maintain said at least two of said cooling procedures active simultaneously.

13. The visual inspection apparatus of claim 12, wherein said visual inspection apparatus is adapted to initiate at least one of said first cooling procedure and said second cooling procedure responsively to each of (a) said sensed temperature indicating output of said first thermal sensor exceeding a first threshold and (b) said sensed temperature indicating output of said second thermal sensor exceeding a second threshold, and wherein said first threshold is different from said second threshold.

14. The visual inspection apparatus of claim 12, wherein said visual inspection apparatus is adapted to initiate at least one of said first cooling procedure and said second cooling procedure responsively to each of (a) said sense (temperature indicating output of said first thermal sensor exceeding a first threshold and (b) said sensed temperature indicating output of said second thermal sensor exceeding a second threshold, wherein said first threshold is different from said second threshold, wherein said visual inspection apparatus further includes a light source bank circuit board and a processing circuit board, wherein said light source bank is carried by said light source bank circuit board and one or more components of said processing circuitry are carried by said processing circuit board, wherein said first thermal sensor is a thermocouple disposed on said light source bank circuit board for sensing of a temperature of said light source bank, and wherein said second thermal sensor is a thermocouple disposed on said processing circuit board for sensing of a temperature of said one or more components of said processing circuitry.

15. A visual inspection apparatus for inspecting an equipment article defining a target substrate, said visual inspection apparatus comprising:
a handset including at least a display and a keyboard and being delimited by a hand held housing to be grasped by an inspector;
a two dimensional image sensor and associated optics for focusing an image of said target substrate onto said two dimensional image sensor, said visual inspection apparatus being adapted so that there can be displayed on said display image data representing light incident on said two dimensional image sensor;
a light source bank for illuminating said target substrate;
first set of thermally conductive heat sink members for removing heat from said light source bank;
image processing circuitry for processing image data representing light incident on said two dimensional image sensor, wherein said light source bank and said image processing circuitry are disposed within said hand held housing;
an elongated inspection tube extending from said handset and being adapted to transmit light generated by said light source bank for illumination of said target substrate;
a thermally conductive heat sink path including one or more heat sink members, said one or more heat sink members forming a thermally conductive path between (a) one or more of said light source bank and components of said image processing circuitry and (b) a location external to said housing subject to being grasped by an inspector, said location external to said housing defining an exposed section of said thermally conductive heat sink path; and
a thermal sensor operationally disposed to sense a temperature of said exposed section of said thermally conductive heat sink path;
wherein said visual inspection apparatus is adapted so that responsively to a temperature indicating output of said thermal sensor said visual inspection apparatus can initiate one or more cooling procedures for cooling of an interior of said hand held housing.

16. The visual inspection apparatus of claim 15, wherein said visual inspection apparatus is adapted to initiate said at least one cooling procedure responsively to a determination that an output of said temperature sensor exceeds a threshold value.

17. The visual inspection apparatus of claim 16, wherein said threshold value is a value determined to indicate that a temperature of said exposed section has reached a value posing a health hazard to an inspector.

18. The visual inspection apparatus of claim 16, wherein said temperature sensor is disposed internal to said hand held housing, and wherein said threshold value is determined empirically prior to use of said visual inspection apparatus for performance of an inspection by correlation of measured temperatures of said exposed section to translated output values output by said temperature sensor disposed within said hand held housing.

19. The visual inspection apparatus of claim 15, wherein said thermally conductive heat path extends between said exposed section and said light source bank, wherein said visual inspection apparatus is further adapted so that said light source bank and said image processing circuitry are maintained in thermally separate relation and wherein said thermally conductive heat sink path does not extend to said image processing circuitry.

* * * * *

UNITED STATES PATENT AND TRADEMARK OFFICE
CERTIFICATE OF CORRECTION

| | |
|---|---|
| PATENT NO. | : 8,310,604 B2 |
| APPLICATION NO. | : 11/925090 |
| DATED | : November 13, 2012 |
| INVENTOR(S) | : James J. Delmonico |

It is certified that error appears in the above-identified patent and that said Letters Patent is hereby corrected as shown below:

Col. 1, Prior to the heading BACKGROUND OF THE INVENTION please insert the following:

-- STATEMENT OF FEDERALLY SPONSORED RESEARCH OR DEVELOPMENT

This invention was made with Government support under Contract No. N68335-06-C-0341 awarded by the Department of the Navy. The Government has certain rights in this invention. --

Signed and Sealed this
Nineteenth Day of February, 2013

Teresa Stanek Rea
*Acting Director of the United States Patent and Trademark Office*